US006986788B2

(12) United States Patent
Paul et al.

(10) Patent No.: US 6,986,788 B2
(45) Date of Patent: Jan. 17, 2006

(54) INTERVERTEBRAL ALLOGRAFT SPACER

(75) Inventors: David C. Paul, Phoenixville, PA (US); Hansjuerg Emch, Philadelphia, PA (US); Beat Schenk, Nuglar (CH)

(73) Assignee: Synthes (U.S.A.), Paoli, PA (US)

( * ) Notice: Subject to any disclaimer, the term of this patent is extended or adjusted under 35 U.S.C. 154(b) by 48 days.

(21) Appl. No.: 09/828,625

(22) Filed: Apr. 9, 2001

(65) Prior Publication Data

US 2001/0049560 A1 Dec. 6, 2001

Related U.S. Application Data

(63) Continuation of application No. 09/363,844, filed on Jul. 30, 1999, now Pat. No. 6,258,125, and a continuation-in-part of application No. 09/219,439, filed on Dec. 23, 1998, now Pat. No. 6,143,033.
(60) Provisional application No. 60/095,209, filed on Aug. 3, 1998, provisional application No. 60/073,271, filed on Jan. 30, 1998, and provisional application No. 60/095,425, filed on Aug. 5, 1998.

(51) Int. Cl.
*A61F 2/44* (2006.01)

(52) U.S. Cl. .................................................. 623/17.11
(58) Field of Classification Search .... 623/16.11–17.16
See application file for complete search history.

(56) References Cited

U.S. PATENT DOCUMENTS

| | | | |
|---|---|---|---|
| 2,621,145 A | 12/1952 | Sano | 167/84 |
| 3,848,601 A | 11/1974 | Ma et al. | 128/305 |
| 4,011,602 A | 3/1977 | Rybicki et al. | 3/1.9 |
| 4,059,115 A | 11/1977 | Jumashev et al. | 128/317 |
| 4,172,128 A | 10/1979 | Thiele et al. | 424/95 |
| 4,222,128 A | 9/1980 | Tomonaga et al. | 3/1.9 |
| 4,237,559 A | 12/1980 | Borom | 3/1.9 |
| 4,294,753 A | 10/1981 | Urist | 260/112 R |
| 4,344,190 A | 8/1982 | Lee et al. | 3/1.9 |
| 4,394,370 A | 7/1983 | Jefferies | 424/15 |
| 4,430,760 A | 2/1984 | Smestad | 3/1.9 |
| 4,440,750 A | 4/1984 | Glowacki et al. | 424/95 |
| 4,472,840 A | 9/1984 | Jefferies | 3/1.9 |
| 4,485,097 A | 11/1984 | Bell | 424/95 |
| 4,501,269 A | 2/1985 | Bagby | 128/92 G |
| 4,610,692 A | 9/1986 | Eitenmuller et al. | 623/16 |
| 4,625,722 A | 12/1986 | Murray | 128/92 VQ |
| 4,627,434 A | 12/1986 | Murray | 128/303 R |
| 4,627,853 A | 12/1986 | Campbell et al. | 623/16 |
| 4,645,503 A | 2/1987 | Lin et al. | 623/16 |

(Continued)

FOREIGN PATENT DOCUMENTS

| | | |
|---|---|---|
| DE | 29 10 627 A1 | 9/1980 |
| DE | 42 42 889 A1 | 6/1994 |
| DE | 44 23 257 A1 | 1/1996 |
| DE | 299 13 200 U1 | 10/1999 |
| EP | 0 366 029 A2 | 5/1990 |

(Continued)

OTHER PUBLICATIONS

Fred H. Albee, *Bone Graft Surgery in Disease, Injury and Deformity*, D. Appleton–Century Company, Inc., New York, 1940, pp. 22, 30, 114, 151, 155, 164, 212, 256–257, 311–313.

(Continued)

*Primary Examiner*—Suzette J-J Gherbi
(74) *Attorney, Agent, or Firm*—Jones Day

(57) ABSTRACT

An allogenic intervertebral implant for fusing vertebrae is disclosed. The implant is a piece of allogenic bone conforming in size and shape with a portion of an end plate of a vertebra. The implant has a wedge-shaped profile to restore disc height and the natural curvature of the spine. The top and bottom surfaces of the implant have a plurality of teeth to resist expulsion and provide initial stability. The implant according to the present invention provides initial stability need for fusion without stress shielding.

58 Claims, 7 Drawing Sheets

U.S. PATENT DOCUMENTS

| | | |
|---|---|---|
| 4,654,464 A | 3/1987 | Mittelmeier et al. ............ 623/16 |
| 4,678,470 A | 7/1987 | Nashef et al. ................. 623/16 |
| 4,728,570 A | 3/1988 | Ashman et al. ............... 428/327 |
| 4,743,259 A | 5/1988 | Bolander et al. .............. 623/16 |
| 4,745,914 A | 5/1988 | Frey et al. ............... 128/92 VP |
| 4,755,184 A | 7/1988 | Silverberg .................... 623/16 |
| 4,781,721 A | 11/1988 | Grundei ....................... 623/16 |
| 4,789,663 A | 12/1988 | Wallace et al. ............... 514/21 |
| 4,834,757 A | 5/1989 | Brantigan .................... 623/17 |
| 4,858,603 A | 8/1989 | Clemow et al. ........ 128/92 ZW |
| 4,863,472 A | 9/1989 | Törmälä et al. ............... 623/16 |
| 4,877,020 A | 10/1989 | Vich ........................ 128/92 V |
| 4,902,296 A | 2/1990 | Bolander et al. .............. 623/16 |
| 4,932,973 A | 6/1990 | Gendler ....................... 623/16 |
| 4,936,848 A | 6/1990 | Bagby .......................... 623/17 |
| 4,950,295 A | 8/1990 | Weigum et al. ............... 623/16 |
| 4,950,296 A | 8/1990 | McIntyre ..................... 623/16 |
| 4,961,740 A | 10/1990 | Ray et al. ..................... 606/61 |
| 4,969,906 A | 11/1990 | Kronman ..................... 623/16 |
| 4,975,526 A | 12/1990 | Kuberasampath et al. .. 530/350 |
| 4,994,084 A | 2/1991 | Brennan ....................... 623/11 |
| 5,026,373 A | 6/1991 | Ray et al. ..................... 606/61 |
| 5,053,049 A | 10/1991 | Campbell ..................... 623/16 |
| 5,061,286 A | 10/1991 | Lyle .............................. 623/16 |
| 5,061,287 A | 10/1991 | Feiler ........................... 623/16 |
| 5,062,850 A | 11/1991 | MacMillan et al. ........... 623/17 |
| 5,067,962 A | 11/1991 | Campbell et al. .............. 623/13 |
| 5,073,373 A | 12/1991 | O'Leary et al. ............ 424/422 |
| 5,078,746 A | 1/1992 | Garner ......................... 623/16 |
| 5,092,887 A | 3/1992 | Gendler ....................... 623/13 |
| 5,092,891 A | 3/1992 | Kummer et al. .............. 623/16 |
| 5,092,892 A | 3/1992 | Ashby .......................... 623/16 |
| 5,092,893 A | 3/1992 | Smith .......................... 623/17 |
| 5,112,354 A | 5/1992 | Sires ............................ 623/16 |
| 5,133,718 A | 7/1992 | Mao ............................. 606/69 |
| 5,133,755 A | 7/1992 | Brekke ......................... 623/16 |
| 5,141,510 A | 8/1992 | Takagi et al. .................. 623/16 |
| 5,152,791 A | 10/1992 | Hakamatsuka et al. ........ 623/16 |
| 5,162,114 A | 11/1992 | Kuberasampath et al. .. 424/423 |
| 5,171,275 A | 12/1992 | Ling et al. .................... 623/16 |
| 5,192,327 A | 3/1993 | Brantigan .................... 623/17 |
| 5,211,664 A | 5/1993 | Tepic et al. ................... 623/16 |
| 5,236,456 A | 8/1993 | O'Leary et al. ............... 623/16 |
| 5,275,954 A | 1/1994 | Wolfinbarger et al. ........ 436/74 |
| 5,281,226 A | 1/1994 | Davydov et al. .............. 606/62 |
| 5,282,861 A | 2/1994 | Kaplan ........................ 623/16 |
| 5,284,655 A | 2/1994 | Bogdansky et al. ......... 424/422 |
| 5,290,558 A | 3/1994 | O'Leary et al. ............ 424/422 |
| 5,298,254 A | 3/1994 | Prewett et al. ............ 424/422 |
| 5,300,077 A | 4/1994 | Howell ......................... 606/96 |
| 5,306,302 A | 4/1994 | Bauer et al. .................. 623/16 |
| 5,306,303 A | 4/1994 | Lynch .......................... 623/16 |
| 5,306,304 A | 4/1994 | Gendler ....................... 623/16 |
| 5,306,308 A | 4/1994 | Gross et al. .................. 623/17 |
| 5,306,309 A | 4/1994 | Wagner et al. ............... 623/17 |
| 5,314,476 A | 5/1994 | Prewett et al. ................ 623/16 |
| 5,320,644 A | 6/1994 | Baumgartner ................ 623/17 |
| 5,329,846 A | 7/1994 | Bonutti ........................ 100/50 |
| 5,366,508 A | 11/1994 | Brekke ......................... 623/16 |
| 5,376,120 A | 12/1994 | Sarver et al. .................. 623/16 |
| 5,383,932 A | 1/1995 | Wilson et al. ................. 623/16 |
| 5,401,269 A | 3/1995 | Buttner-Janz et al. ..... 623/17.11 |
| 5,405,390 A | 4/1995 | O'Leary et al. ............... 623/16 |
| 5,405,391 A | 4/1995 | Hednerson et al. ........... 623/17 |
| 5,423,817 A | 6/1995 | Lin .............................. 606/61 |
| 5,425,768 A | 6/1995 | Carpenter et al. ............. 623/6 |
| 5,425,769 A | 6/1995 | Snyders, Jr. .................. 623/16 |
| 5,425,770 A | 6/1995 | Piez et al. .................... 623/16 |
| 5,425,772 A | 6/1995 | Brantigan .................... 623/17 |
| 5,433,751 A | 7/1995 | Christel et al. ............... 623/16 |
| 5,439,684 A | 8/1995 | Prewett et al. ............ 424/422 |
| 5,443,514 A | 8/1995 | Steffee ......................... 623/17 |
| 5,458,638 A | 10/1995 | Kuslich et al. ............... 623/17 |
| 5,484,437 A * | 1/1996 | Michelson ................... 606/61 |
| 5,484,601 A | 1/1996 | O'Leary et al. ............ 424/422 |
| 5,489,307 A | 2/1996 | Kuslich et al. ............... 623/17 |
| 5,489,308 A | 2/1996 | Kuslich et al. ............... 623/17 |
| 5,492,697 A | 2/1996 | Boyan et al. ............... 424/422 |
| 5,501,706 A | 3/1996 | Arenberg ..................... 623/16 |
| 5,507,813 A | 4/1996 | Dowd et al. ................. 623/16 |
| 5,510,396 A | 4/1996 | Prewett et al. ............... 523/113 |
| 5,514,180 A | 5/1996 | Heggeness et al. ........... 623/17 |
| 5,516,532 A | 5/1996 | Atala et al. ................. 424/548 |
| 5,522,899 A | 6/1996 | Michelson ................... 623/17 |
| 5,531,791 A | 7/1996 | Wolfinbarger, Jr. .......... 623/16 |
| 5,534,030 A | 7/1996 | Navarro et al. ............... 623/17 |
| 5,545,222 A | 8/1996 | Bonutti ........................ 623/11 |
| 5,549,679 A | 8/1996 | Kuslich ........................ 623/17 |
| 5,554,191 A | 9/1996 | Lahille et al. ................ 623/17 |
| 5,554,192 A | 9/1996 | Crowninshield ............. 623/16 |
| 5,556,379 A | 9/1996 | Wolfinbarger ................ 604/49 |
| 5,556,430 A | 9/1996 | Gendler ....................... 623/16 |
| 5,569,308 A | 10/1996 | Sottosanti ................... 623/165 |
| 5,570,706 A | 11/1996 | Howell ....................... 128/898 |
| 5,571,190 A | 11/1996 | Ulrich et al. ................. 623/17 |
| 5,571,192 A | 11/1996 | Schönhöffer ................. 623/17 |
| 5,585,116 A | 12/1996 | Boniface et al. ............ 424/549 |
| 5,591,235 A | 1/1997 | Kuslich ........................ 623/17 |
| 5,593,409 A | 1/1997 | Michelson ................... 606/61 |
| 5,603,716 A | 2/1997 | Morgan et al. ............... 606/88 |
| 5,607,474 A | 3/1997 | Athanasiou et al. .......... 623/11 |
| 5,609,635 A | 3/1997 | Michelson ................... 623/17 |
| 5,609,636 A | 3/1997 | Kohrs et al. ................. 623/17 |
| 5,609,637 A | 3/1997 | Biedermann et al. ......... 623/17 |
| 5,645,598 A | 7/1997 | Brosnahan, III ............. 623/17 |
| 5,658,337 A | 8/1997 | Kohrs et al. ................. 623/17 |
| 5,658,351 A | 8/1997 | Dudasik et al. ............... 623/23 |
| 5,665,120 A | 9/1997 | Ohtsuka et al. ............... 623/16 |
| 5,676,699 A | 10/1997 | Gogolewski et al. ......... 623/16 |
| 5,683,394 A | 11/1997 | Rinner ........................ 606/86 |
| 5,683,463 A | 11/1997 | Godefroy et al. ............. 623/17 |
| 5,683,464 A | 11/1997 | Wagner et al. ............... 623/17 |
| 5,697,981 A | 12/1997 | Ison et al. .................... 623/16 |
| 5,702,449 A | 12/1997 | McKay ........................ 623/17 |
| 5,702,453 A | 12/1997 | Rabbe et al. ................. 623/17 |
| 5,702,455 A | 12/1997 | Saggar ........................ 623/17 |
| 5,709,683 A | 1/1998 | Bagby ......................... 606/61 |
| 5,716,415 A * | 2/1998 | Steffee ..................... 623/16.11 |
| 5,722,977 A | 3/1998 | Wilhelmy ..................... 606/84 |
| 5,725,579 A | 3/1998 | Fages et al. .................. 623/16 |
| 5,725,813 A | 3/1998 | Nies ............................. 264/15 |
| 5,728,159 A | 3/1998 | Stroever et al. ............... 623/16 |
| 5,733,288 A | 3/1998 | Allen ........................... 606/79 |
| 5,741,253 A | 4/1998 | Michelson ................... 606/61 |
| 5,741,261 A | 4/1998 | Moskovitz et al. ........... 606/79 |
| 5,755,793 A | 5/1998 | Smith et al. .................. 623/16 |
| 5,766,252 A | 6/1998 | Henry et al. .................. 623/17 |
| 5,766,253 A | 6/1998 | Brosnahan, III ............. 623/17 |
| 5,769,897 A | 6/1998 | Härle .......................... 623/16 |
| 5,776,197 A | 7/1998 | Rabbe et al. ................. 623/17 |
| 5,776,198 A | 7/1998 | Rabbe et al. ................. 623/17 |
| 5,776,199 A | 7/1998 | Michelson ................... 623/17 |
| 5,782,830 A | 7/1998 | Farris .......................... 606/61 |
| 5,782,915 A | 7/1998 | Stone .......................... 623/11 |
| 5,782,917 A | 7/1998 | Carn ............................ 623/16 |
| 5,785,710 A | 7/1998 | Michelson ................... 606/61 |
| 5,785,714 A | 7/1998 | Morgan et al. ............... 606/86 |
| 5,797,871 A | 8/1998 | Wolfinbarger, Jr. .......... 604/49 |
| 5,798,096 A | 8/1998 | Pavlyk ...................... 424/78.35 |
| 5,814,084 A | 9/1998 | Grivas et al. ................. 623/16 |
| 5,820,581 A | 10/1998 | Wolfinbarger, Jr. .......... 604/49 |
| 5,824,078 A | 10/1998 | Nelson et al. ................. 623/66 |
| 5,824,084 A | 10/1998 | Muschler ..................... 623/16 |
| 5,824,088 A | 10/1998 | Kirsch .......................... 623/16 |
| 5,861,043 A | 1/1999 | Carn ............................ 623/16 |
| 5,865,845 A | 2/1999 | Thalgott ....................... 623/17 |
| 5,865,848 A | 2/1999 | Baker .......................... 623/17 |
| 5,865,849 A | 2/1999 | Stone .......................... 623/18 |
| 5,868,749 A | 2/1999 | Reed ............................ 606/76 |
| 5,876,455 A | 3/1999 | Harwin ........................ 623/16 |

| | | | | | | |
|---|---|---|---|---|---|---|
| 5,879,403 A | 3/1999 | Ostiguy et al. ............... 623/22 | | 2001/0016777 A1 | 8/2001 | Biscup ................... 623/17.16 |
| 5,885,292 A | 3/1999 | Moskovitz et al. ........... 606/79 | | 2002/0091447 A1 | 7/2002 | Shimp et al. ............ 623/17.16 |
| 5,885,299 A | 3/1999 | Winslow et al. ............... 606/99 | | 2002/0106393 A1 | 8/2002 | Bianchi et al. ............. 424/423 |
| 5,888,222 A | 3/1999 | Coates et al. ................. 623/17 | | 2002/0107570 A1 | 8/2002 | Sybert et al. ............ 623/13.17 |
| 5,888,224 A | 3/1999 | Beckers et al. ............... 623/17 | | | | |
| 5,888,227 A * | 3/1999 | Cottle ..................... 623/17.11 | | FOREIGN PATENT DOCUMENTS | | |
| 5,895,426 A | 4/1999 | Scarborough et al. ........ 623/17 | | | | |
| 5,897,593 A | 4/1999 | Kohrs et al. .................. 623/17 | | EP | 0 505 634 A1 | 9/1992 |
| 5,899,939 A * | 5/1999 | Boyce et al. ............ 623/16.11 | | EP | 0 517 030 A2 | 12/1992 |
| 5,899,941 A | 5/1999 | Nishijima et al. ............. 623/17 | | EP | 0 520 237 A2 | 12/1992 |
| 5,902,338 A | 5/1999 | Stone ........................... 623/13 | | EP | 0 538 183 | 4/1993 |
| 5,904,716 A | 5/1999 | Gendler ....................... 623/11 | | EP | 0 577 178 A1 | 1/1994 |
| 5,904,719 A | 5/1999 | Errico et al. .................. 623/17 | | EP | 0 639 351 A2 | 2/1995 |
| 5,910,315 A | 6/1999 | Stevenson et al. .......... 424/422 | | EP | 0 646 366 A1 | 4/1995 |
| 5,913,900 A | 6/1999 | Stone .......................... 623/20 | | EP | 0 966 930 A1 | 12/1999 |
| 5,919,196 A | 7/1999 | Bobic et al. .................. 606/86 | | FR | 2645748 | 10/1990 |
| 5,922,027 A | 7/1999 | Stone ........................... 623/11 | | FR | 2 552 659 | 2/1995 |
| 5,935,169 A | 8/1999 | Chan ........................... 623/16 | | FR | 2 717 068 | 9/1995 |
| 5,944,755 A | 8/1999 | Stone ........................... 623/16 | | GB | 2 220 571 A | 1/1990 |
| 5,968,047 A | 10/1999 | Reed ........................... 606/76 | | JP | 178993 | 7/1988 |
| 5,968,098 A | 10/1999 | Winslow ..................... 623/17 | | JP | 064099 | 9/1990 |
| 5,972,034 A | 10/1999 | Hofmann et al. ............. 623/23 | | JP | 093100 | 11/1990 |
| 5,972,368 A | 10/1999 | McKay ....................... 424/423 | | JP | 165740 | 2/1991 |
| 5,976,187 A | 11/1999 | Richelsoph ................. 623/17 | | JP | 6-14947 | 1/1994 |
| 5,980,522 A | 11/1999 | Koros et al. .................. 606/61 | | SU | 833226 B * | 5/1981 |
| 5,981,828 A | 11/1999 | Nelson et al. ................. 623/16 | | SU | 1465040 | 3/1989 |
| 5,984,922 A | 11/1999 | McKay ........................ 606/61 | | WO | WO 94/26211 | 11/1994 |
| 5,984,967 A | 11/1999 | Zdeblick et al. .............. 623/17 | | WO | WO 94/26213 | 11/1994 |
| 5,989,289 A | 11/1999 | Coates et al. ................. 623/17 | | WO | WO 95/08964 | 4/1995 |
| 5,990,382 A | 11/1999 | Fox ............................. 623/16 | | WO | WO 95/15133 | 6/1995 |
| 5,997,580 A | 12/1999 | Mastrorio et al. ............. 623/22 | | WO | WO 96/11642 | 4/1996 |
| 5,997,581 A | 12/1999 | Khalili ......................... 623/23 | | WO | WO 96/39988 | 12/1996 |
| 6,005,161 A | 12/1999 | Brekke et al. ................. 623/16 | | WO | WO 97/14378 | 4/1997 |
| 6,008,433 A | 12/1999 | Stone ........................... 623/16 | | WO | WO 97/15248 | 5/1997 |
| 6,013,853 A | 1/2000 | Athanasiou et al. .......... 623/11 | | WO | WO 97/25945 | 7/1997 |
| 6,025,538 A | 2/2000 | Yaccarino, III .............. 623/16 | | WO | WO 97/32547 | 9/1997 |
| 6,030,635 A | 2/2000 | Gertzman et al. .......... 424/423 | | WO | WO 98/17209 | 4/1998 |
| 6,033,405 A | 3/2000 | Winslow et al. ............... 606/61 | | WO | WO 98/55052 | 12/1998 |
| 6,033,438 A | 3/2000 | Bianchi et al. ................ 623/17 | | WO | WO 98/56319 | 12/1998 |
| 6,039,762 A | 3/2000 | McKay ........................ 623/17 | | WO | WO 98/56433 | 12/1998 |
| 6,045,554 A | 4/2000 | Grooms et al. ............... 606/73 | | WO | WO 99/09914 | 3/1999 |
| 6,045,579 A | 4/2000 | Hochshuler et al. .......... 623/17 | | WO | WO 99/13806 | 3/1999 |
| 6,045,580 A | 4/2000 | Scarborough et al. ........ 623/17 | | WO | WO 99/29271 | 6/1999 |
| 6,049,025 A | 4/2000 | Stone et al. ................... 623/16 | | WO | WO 99/32055 | 7/1999 |
| 6,053,916 A | 4/2000 | Moore .......................... 606/61 | | WO | WO 99/38461 | 8/1999 |
| 6,059,790 A | 5/2000 | Sand et al. ..................... 606/99 | | WO | WO 00/07527 | 2/2000 |
| 6,080,158 A * | 6/2000 | Lin .............................. 606/61 | | WO | WO 00/07528 | 2/2000 |
| 6,080,193 A | 6/2000 | Hochshuler et al. .......... 623/17 | | WO | WO 00/30568 | 6/2000 |
| 6,090,998 A | 7/2000 | Grooms et al. ............... 623/16 | | WO | WO 00/40177 | 7/2000 |
| 6,096,080 A | 8/2000 | Nicholson et al. ............ 623/17 | | WO | WO 00/40179 | 7/2000 |
| 6,096,081 A | 8/2000 | Grivas et al. ............. 623/17.11 | | WO | WO 00/41654 | 7/2000 |
| 6,110,482 A | 8/2000 | Khouri et al. ............... 424/423 | | WO | WO 00/42954 | 7/2000 |
| 6,111,164 A | 8/2000 | Rainey et al. ................. 623/16 | | WO | WO 00/59412 | 10/2000 |
| 6,123,731 A | 9/2000 | Boyce et al. ............ 623/23.63 | | WO | WO 00/74607 | 12/2000 |
| 6,143,030 A | 11/2000 | Schroder ................. 623/16.11 | | WO | WO 00/74608 | 12/2000 |
| 6,143,033 A | 11/2000 | Paul et al. ................. 623/17.11 | | WO | WO 01/8611 A1 | 2/2001 |
| 6,156,070 A | 12/2000 | Incavo et al. ............ 623/23.52 | | | | |
| 6,174,311 B1 * | 1/2001 | Branch et al. ................. 606/61 | | | | |
| 6,187,329 B1 | 2/2001 | Agrawal et al. ............ 424/426 | | OTHER PUBLICATIONS | | |
| 6,200,347 B1 | 3/2001 | Anderson et al. ........ 623/16.11 | | | | |
| 6,206,923 B1 | 3/2001 | Boyd et al. ................ 623/17.11 | | | | |
| 6,241,769 B1 | 6/2001 | Nicholson et al. ....... 623/17.11 | | | | |
| 6,245,108 B1 | 6/2001 | Biscup ..................... 623/17.11 | | | | |
| 6,258,125 B1 | 7/2001 | Paul et al. ................. 623/17.11 | | | | |
| 6,261,586 B1 | 7/2001 | McKay ....................... 424/423 | | | | |
| 6,270,528 B1 | 8/2001 | McKay ..................... 623/17.11 | | | | |
| 6,277,149 B1 | 8/2001 | Boyle et al. ............ 623/17.16 | | | | |
| 6,371,988 B1 | 4/2002 | Pafford et al. ............ 623/17.11 | | | | |
| 6,482,233 B1 * | 11/2002 | Aebi et al. ................. 623/17.11 | | | | |
| 6,494,883 B1 | 12/2002 | Ferree .......................... 606/61 | | | | |
| 6,511,509 B1 | 1/2003 | Ford et al. ................. 623/23.5 | | | | |
| 6,554,863 B2 | 4/2003 | Paul et al. ................. 623/17.11 | | | | |
| 2001/0001129 A1 | 5/2001 | McKay et al. ........... 623/17.16 | | | | |
| 2001/0010021 A1 | 7/2001 | Boyd et al. ............... 623/17.13 | | | | |
| 2001/0014831 A1 | 8/2001 | Scarborough ............ 623/23.51 | | | | |
| 2001/0016775 A1 | 8/2001 | Scarborough et al. ... 623/17.16 | | | | |

Fred H. Albee, "Bone Surgery With Machine Tools," *Scientific American*, Apr., 1936, pp. 178–181.

Fred H. Albee, *Bone–Graft Surgery*, W. B. Saunders Company, Philadelphia, Pennsylvania, 1915, pp. 145, 165–166, 171, 368–369.

Shrikar Bondre et al., "Biodegradable Foam Coating of Cortical Allografts," *Tissue Engineering*, vol. 6, pp. 217–227, 2000.

Kai–Uwe Lewandrowski, "Improvement of Incorporation of Bone Allografts," CRISP grant abstract, Fiscal Year 2000.

Joseph Catanese III et al., "Heterogeneity of the mechanical properties of demineralized bone," *Journal of Biomechanics*, vol. 32, pp. 1365–1369, 1999.

L. Wolfinbarger, Jr. et al., "Processing Factors Contributing to Production of Maximally Osteoinductive Demineralised Ground Bone for Use in Orthopaedic of Periodontal Applications," Advances in Tissue Banking (Singapore: World Scientific Publishing Co., 1999), pp. 125–145.

Steven C. Ludwig et al., "Osteoinductive Bone Graft Substitutes for Spinal Fusion," *Orthopedic Clinics of North America*, vol. 30, pp. 635–645, 1999.

Jon E. Block et al., "Spine Fusion With Demineralized Bone," *J. Neorosurg.*, vol. 88, pp. 354–356, 1998.

Kai–Uwe Lewandrowski et al., "Mechanical Properties of Perforated and Partially Demineralized Bone Grafts," *Clinical Orthopaedics and Related Research*, No. 353, pp. 238–246, 1998.

Min Zhang et al., "Effects(s) of the Demineralization Process on the Osteoinductivity of Demineralized Bone Matrix," *J. Periodontol.*, vol. 68, pp. 1085–1092, 1997.

Kai–Uwe Lewandrowski et al., "Improved Osteoinduction of Cortical Bone Allografts: A Study of the Effects of Laser Perforation and Partial Demineralization," *Journal of Orthopaedic Research*, vol. 15, pp. 748–756, 1997.

Kai–Uwe Lewandrowski et al., "Kinetics of cortical bone demineralization: Controlled demineralization—a new method for modifying cortical bone allografts," *Journal of Biomedical Materials Research*, vol. 31, pp. 365–372, 1996.

Douglas W. Jackson et al., "Biological Remodeling after Anterior Cruciate Ligament Reconstruction Using a Collagen Matrix Derived from Demineralized Bone," *American Journal of Sports Medicine*, vol. 24, pp. 405–414, 1996.

Steven M. Bowman et al., "The Tensile Behavior of Demineralized Bovine Cortical Bone," *J. Biomechanics*, vol. 29, pp. 1497–1501, 1996.

K.K.J. Hallfeldt et al., "Sterilization of Partially Demineralized Bone Matrix: The Effects of Different Sterilization Techniques on Osteogenetic Properties," *Journal of Surgical Research*, vol. 59, pp. 614–620, 1995.

Kai–Uwe Lewandrowski et al., "Flexural Rigidity in Partially Demineralized Diaphyseal Bone Grafts," *Clinical Orthopaedics and Related Research*, No. 317, pp. 254–262, 1995.

J.J. Broz et al., "Material and Compositional Properties of Selectively Demineralized Cortical Bone," *J. Biomechanics*, vol. 28, pp. 1357–1368, 1995.

Howard S. An et al., "Comparison Between Allograft Plus Demineralized Bone Matrix Versus Autograft in Anterior Cervical Fusion. A Prospective Multicenter Study," *SPINE*, vol. 20, pp. 2211–2216, 1995.

Samuel S. Jorgenson, "A Prospective Analysis of Autograft Versus Allograft in Posterolateral Lumbar Fusion in the Same Patient," *SPINE*, vol. 19, pp. 2048–2053, 1994.

Michael Centrella., "Transforming Growth Factor–β Gene Family Members and Bone," *Endocrine Reviews*, vol. 15, pp. 27–39, 1994.

Norbert Kübler et al., "Osteoinductive, Morphologic, and Biomechanical Properties of Autolyzed, Antigen–Extracted, Allogenic Human Bone," *J. Oral Maxillofac. Surg.*, vol. 51, pp. 1346–1357, 1993.

Stephen E. Fucini et al., "Small Versus Large Particles of Demineralized Freeze–Dried Bone Allografts in Human Intrabony Periodontal Defects," *J. Periodontol.*, vol. 64, pp. 844–847, 1993.

Abraham Nimrod et al., "Absorption, Distribution, Metabolism, and Excretion of Bacteria–Derived Hyaluronic Acid in Rats and Rabbits," *Journal of Occular Pharmacology*, vol. 8, pp. 161–172, 1992.

Torvard C. Laurent et al., "Hyaluronan," *The FASEB Journal*, vol. 6, pp. 2397–2404, 1992.

Christian Delloye et al., "Morphometric and Physical Investigations of Segmental Cortical Bone Autografts and Allografts in Canine Ulnar Defects," *Clinical Orthopaedics and Related Research*, No. 282, pp. 273–292, 1992.

Ma Zhen Guo et al., "The Mechanical and Biological Properties of Demineralised Cortical Bone Allografts in Animals," *The Journal of Bone and Joint Surgery [Br]*, vol. 73–B, pp. 791–794, 1991.

Anthony J. Celeste et al., "Identification of transforming growth factor β family members present in bone–inductive protein purified from bovine bone," *Proc. Natl. Acad. Sci. USA*, vol. 87, pp. 9843–9847, 1990.

Stanley G. Hopp et al., "A Study of the Mechanical Strength of Long Bone Defects Treated with Various Bone Autograft Substitutes: An Experimental Investigation in the Rabbit," *Journal of Orthopaedic Research*, vol. 7, pp. 579–584, 1989.

Reuven Gepstein et al., "Bridging Large Defects in Bone by Demineralized Bone Matrix in the Form of a Powder," *The Journal of Bone and Joint Surgery*, vol. 69–A, pp. 984–992, 1987.

Laurence E. Dahners et al., "Long Bone Defects Treated With Demineralized Bone," *Southern Medical Journal*, vol. 78, pp. 933–934, 1985.

Julie Glowacki et al., "Demienralized Bone Implants," *Clinics in Plastic Surgery*, vol. 12, pp. 233–241, 1985.

Marshall R. Urist et al., "Bone Cell Differentiation and Growth Factors," *Science*, vol. 220, pp. 680–686, 1983.

J.J. Vandersteenhoven et al., "Histological investigation of bone induction by demineralized allogenic bone matrix: A natural biomaterial for osseous reconstruction," *Journal of Biomedical Materials Research*, vol. 17, pp. 1003–1014, 1983.

P.J. Makarewicz et al., "Kinetics of Acid Diffusion and Demineralization of Bone," *The Journal of Photographic Science*, vol. 28, pp. 177–184, 1980.

F. M. Eggert et al., "Rapid Demineralization in Acidic Buffers," *Histochemistry*, vol. 59, pp. 215–224, 1979.

S. M. Tuli et al., "The Osteoinductive Property of Decalcified Bone Matrix. An Experimental Study," *The Journal of Bone and Joint Surgery*, vol. 60–B, pp. 116–123, 1978.

Albert H. Burstein et al., "Contribution of Collagen and Mineral to the Elastic–Plastic Properties of Bone," *The Journal of Bone and Joint Surgery*, vol. 57–A, pp. 956–961, 1975.

A. H. Reddi et al., "Chemical Sequences in the Transformation of Normal Fibroblasts in Adolescent Rats," *Proc. Nat. Acad. Sci. USA*, vol. 69, pp. 1601–1605, 1972.

Marshall R. Urist, "Surface–Decalcified Aoolgeneic Bone (SDAB) Implants. A Preliminary Report of 10 Cases and 25 Comparable Operations With Undecalcified Lyophilized Bone Implants.," *Clinical Orthopaedics and Related Research*, No. 56, pp. 37–50, 1968.

Marshall R. Urist, "Bone Formation by Autoinduction," *Science*, pp. 893–899, vol. 150, 1965.

\* cited by examiner

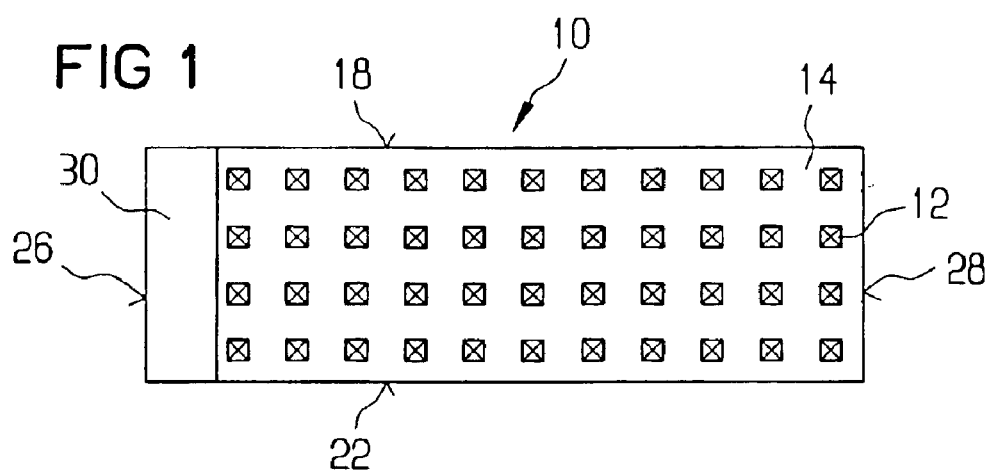
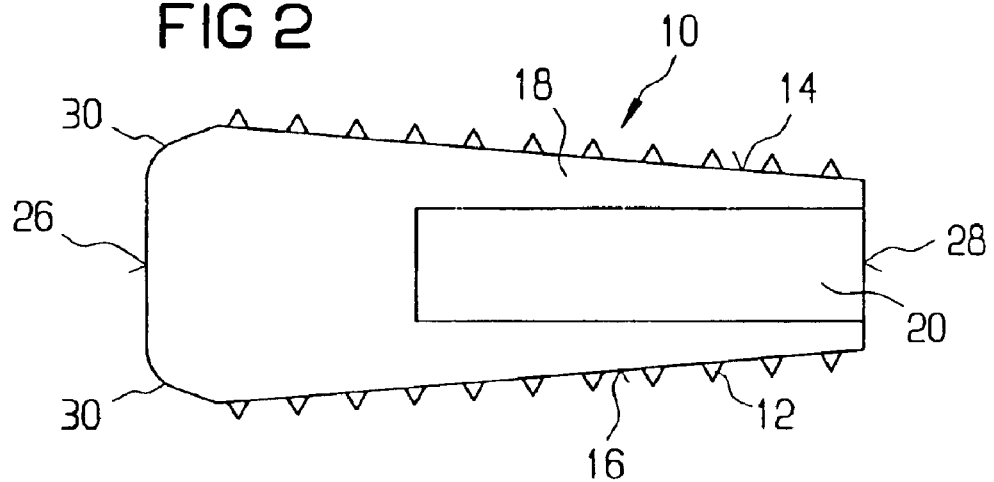
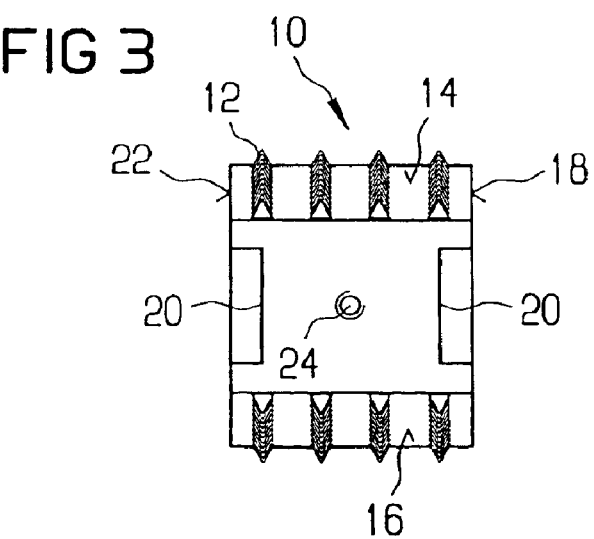

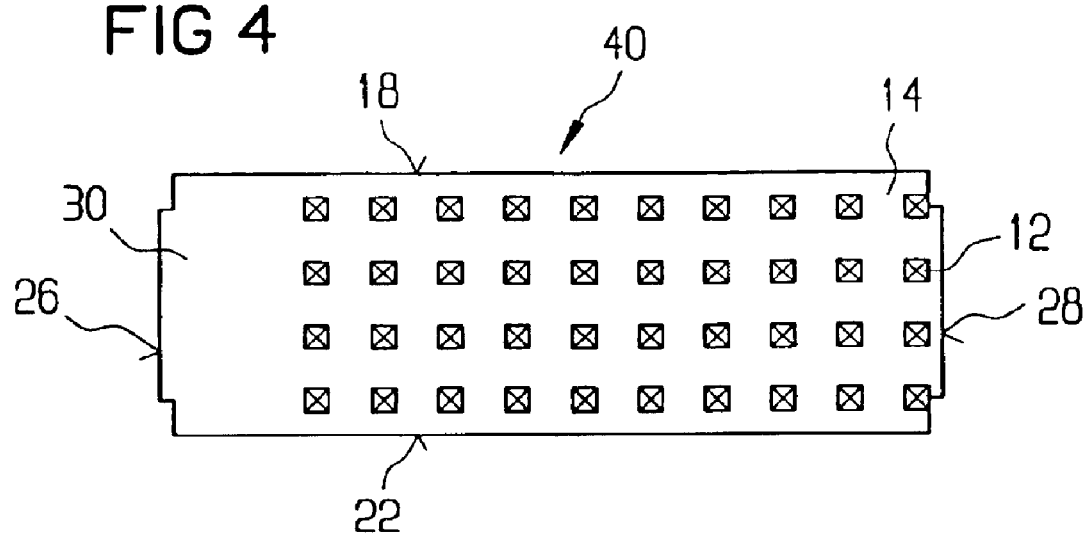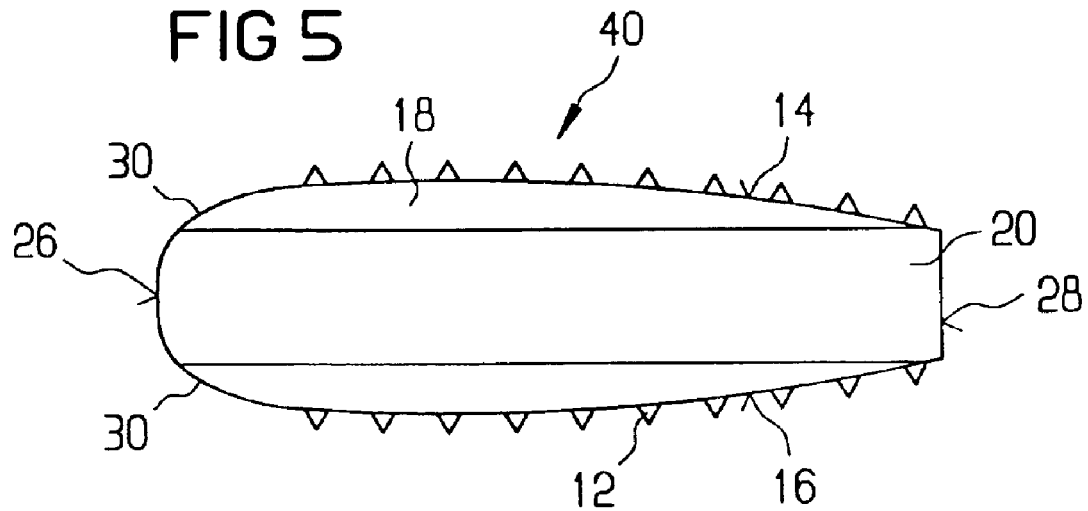

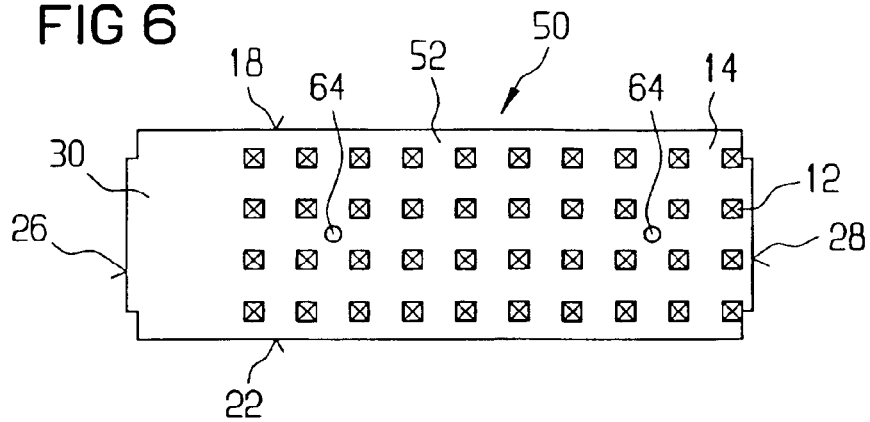
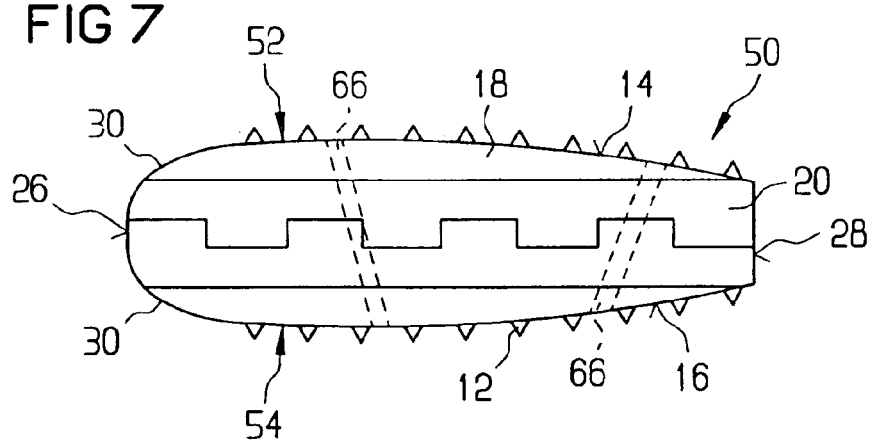
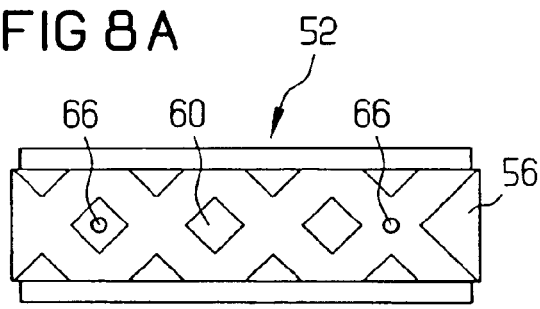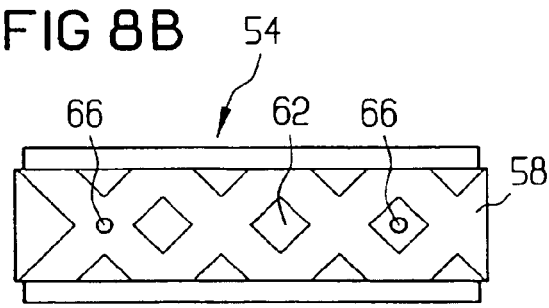

INTERVERTEBRAL ALLOGRAFT SPACER

CROSS-REFERENCE TO RELATED APPLICATIONS

This is a continuation of U.S. patent application Ser. No. 09/363,844, filed Jul. 30, 1999, now U.S. Pat. No. 6,258,125, which claims the benefit under 35 U.S.C. § 119(e) of Provisional Application No. 60/095,209, filed Aug. 3, 1998, and is a continuation-in-part of U.S. patent application Ser. No. 09/219,439, filed Dec. 23, 1998, now U.S. Pat. No. 6,143,033, which in turn claims the benefit under 35 U.S.C. § 119(e) of Provisional Application No. 60/073,271, filed on Jan. 30, 1998 and Provisional Application No. 60/095,425, filed on Aug. 5, 1998. The entire content of each of these applications is expressly incorporated herein by reference thereto.

FIELD OF THE INVENTION

The present invention is directed to an allogenic implant and, more particularly, to an allogenic intervertebral implant.

BACKGROUND OF THE INVENTION

A number of medical conditions such as compression of spinal cord nerve roots, degenerative disc disease, and spondylolisthesis can cause severe low back pain. Intervertebral fusion is a surgical method of alleviating low back pain. In posterior lumbar interbody fusion ("PLIF"), two adjacent vertebral bodies are fused together by removing the affected disc and inserting an implant that would allow for bone to grow between the two vertebral bodies to bridge the gap left by the disc removal.

A number of different implants and implant materials have been used in PLIF with varying success. Current implants used for PLIF include threaded titanium cages and allografts. Threaded titanium cages suffer from the disadvantage of requiring drilling and tapping of the vertebral end plates for insertion. In addition, the incidence of subsidence in long term use is not known. Due to MRI incompatibility of titanium, determining fusion is problematic. Finally, restoration of lordosis, i.e., the natural curvature of the lumbar spine is very difficult when a cylindrical titanium cage is used.

Allografts are sections of bone taken from a long bone of a donor. A cross section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They are also MRI compatible so that fusion can be more accurately ascertained and promote the formation of bone, i.e., osteoconductive. Although the osteoconductive nature of the allograft provides a biological interlocking between the allograft and the vertebrae for long term mechanical strength, initial and short term mechanical strength of the interface between the allograft and the vertebrae are lacking as evidenced by the possibility of the allograft being expelled after implantation.

Currently commercially available allografts are simply sections of bone not specifically designed for use in PLIF. As a result, the fusion of the vertebral bodies does not occur in optimal anatomical position. A surgeon may do some minimal intraoperative shaping and sizing to customize the allograft for the patient's spinal anatomy. However, significant shaping and sizing of the allograft is not possible due to the nature of the allograft. Even if extensive shaping and sizing were possible, a surgeon's ability to manually shape and size the allograft to the desired dimensions is severely limited.

Most PLIF implants, whether threaded cages or allograft, are available in different sizes and have widths that vary with the implant height. For example, the width of a cylindrical cages will be substantially equivalent to the height. Although larger heights may be clinically indicated, wider implants are generally not desirable since increased width requires removal of more of the facet, which can lead to decreases stability, and more retraction of nerve roots, which can lead to temporary or permanent nerve damage.

As the discussion above illustrates, there is a need for an improved implant for fusing vertebrae.

SUMMARY OF THE INVENTION

The present invention relates to an allogenic intervertebral implant for use when surgical fusion of vertebral bodies is indicated. The implant comprises a piece of allogenic bone conforming in size and shape with a portion of an end plates of the vertebrae and has a wedge-shaped profile with a plurality of teeth located on top and bottom surfaces. The top and bottom surfaces can be flat planar surfaces or curved surfaces to mimic the topography of the end plates. The implant has a channel on at least one side for receiving a surgical tool. This channel runs in the anterior direction to accommodate a variety of surgical approaches. A threaded hole on the anterior, posterior, posterior-lateral, or lateral side can be provided for receiving a threaded arm of an insertion tool.

In another embodiment, the implant has an interior space for receiving an osteoconductive material to promote the formation of new bone.

In another embodiment, the implant is made of a plurality of interconnecting sections with mating sections. Preferably, the implant is made in two halves: a top portion having a top connecting surface and a bottom portion having a bottom connecting surface. The top connecting surface mates with the bottom connecting surface when the top and bottom portions are joined. The top and bottom portions have holes that align for receiving a pin to secure the top and bottom portions together. The pin can be made of allogenic bone.

In a different embodiment, the medial side of the implant has a scalloped edge such that when a first implant is implanted with a second implant with the medial sides facing each other, the scalloped edges define a cylindrical space.

The present invention also relates to a discrete spacer used in conjunction with any of the other embodiments of the implant. The spacer comprises a piece of allogenic bone conforming in size and shape with a portion of an end plates of the vertebrae and has a wedge-shaped profile with substantially smooth top and bottom surfaces. The intersecting regions between the top and bottom surfaces and at least one of the lateral sides and the intersecting regions between the anterior and posterior sides and the same lateral side are curved surfaces to facilitate implantation of the spacer. Thus, the spacer can be implanted through an opening on one side of the spinal canal and moved with a surgical instrument to the contralateral side.

BRIEF DESCRIPTION OF THE DRAWINGS

FIG. 1 is a top view of a first embodiment of the implant according to the present invention;

FIG. 2 is a side view of the implant of FIG. 1;

FIG. 3 is a back view of the implant of FIG. 1;

FIG. 4 is a top view of a second embodiment of the implant;

FIG. 5 is a side view of the implant of FIG. 4;

FIG. 6 is a top view of a third embodiment of the implant;

FIG. 7 is a side view of the implant of FIG. 6;

FIG. 8A is a top view of a top connecting surface of a top portion of the implant of FIG. 6;

FIG. 8B is a top view of a bottom connecting surface of a bottom portion of the implant of FIG. 6;

DESCRIPTION OF THE PREFERRED EMBODIMENTS

Figure 10A:
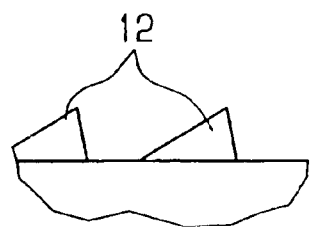
FIG. 10A is a side view of one embodiment of the teeth on the implant.
Figure 10B:
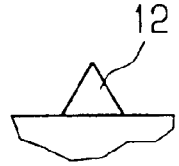
FIG. 10B is a side view of a second embodiment of the teeth of the implant.

FIG. 1 shows a top view of a first embodiment of intervertebral allograft spacer or implant 10 according to the present invention. Implant 10 conforms in size and shape with a portion of end plates of the vertebrae between which implant 10 is to be implanted. Because implant 10 is an allograft, implant 10 promotes the formation of new bone to fuse the two vertebral bodies together. Although implant 10 will probably be predominantly used in the lumbar region of the spine, implant 10 can be configured for implantation in any region of the spine. Implant 10 has a plurality of teeth 12 on superior and inferior surfaces 14, 16 which provide a mechanical interlock between implant 10 and the end plates. Teeth 12 provide the mechanical interlock by penetrating the end plates. The initial mechanical stability afforded by teeth 12 minimizes the risk of post-operative expulsion of implant 10. Teeth 12 can be pyramid-shaped (FIG. 10A). Preferably, the angle formed from the tip to the base is approximately 60°. Alternatively, teeth 12 have a saw tooth shape with the saw tooth running in the anterior-posterior direction (FIG. 10B).

Figure 9:
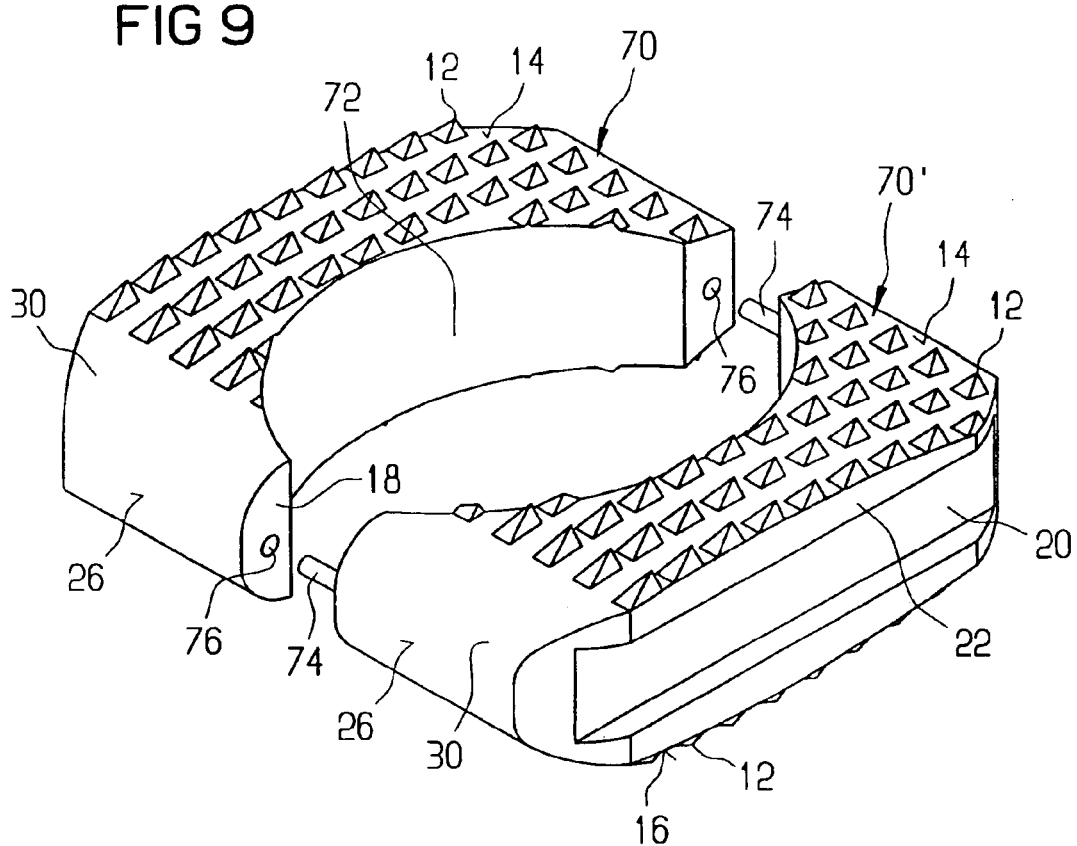
FIG. 9 is a perspective view of a fourth embodiment of the implant.

As shown in FIG. 2 and FIG. 3, a first lateral side 18 has a channel 20 and a second lateral side 22 also has a channel 20. Channels 20 are sized to receive a surgical instrument such as an inserter for implantation of implant 10. If the inserter has a threaded arm, implant 10 can be provided with a threaded hole 24. In FIG. 2, channel 20 is shown extended only partially along first lateral side 18. Channel 20 can extend along the entire length of first lateral side 18 as shown in the embodiment of FIG. 5. In FIG. 3, channels 20 are shown on both first and second lateral sides 18, 22. It should be noted that implant 10 can also have no channels or channels on one lateral side only as shown in the embodiment of FIG. 9.

The dimensions of implant 10 can be varied to accommodate a patient's anatomy. Typically, implant 10 would have a width between 6–15 mm (in the medial-lateral direction), a length between 15–30 mm (in the anterior-posterior direction), and a height between 4–30 mm (maximum height in the superior-inferior direction). The size of implant 10 allows implant 10 to be implanted using conventional open surgical procedures or minimally invasive procedures, such as laparoscopic surgery. Additionally, because the width is kept to a restricted size range and does not necessarily increase with implant height, taller implants can be used without requiring wider implants. Thus, facet removal and retraction of nerve roots can remain minimal.

In order to restore the natural curvature of the spine after the affected disc has been removed, implant 10 has a wedge-shaped profile. As shown in FIG. 2, this wedge shape results from a gradual decrease in height from an anterior side 26 to a posterior side 28. In anatomical terms, the natural curvature of the lumbar spine is referred to as lordosis. When implant 10 is to be used in the lumbar region, the angle formed by the wedge should be approximately between 4.2° and 15° so that the wedge shape is a lordotic shape which mimics the anatomy of the lumbar spine.

In order to facilitate insertion of implant 10, anterior side 26 transitions to superior and inferior surfaces 14, 16 with rounded edges 30. Rounded edges 30 enable implant 10 to slide between the end plates while minimizing the necessary distraction of the end plates.

Although implant 10 is typically a solid piece of allogenic bone, implant 10 can be provided with a hollow interior to form an interior space. This interior space can be filled with bone chips or any other osteoconductive material to further promote the formation of new bone.

FIG. 4 shows a top view of a second embodiment of an implant 40 according to the present invention. In general, most of the structure of implant 40 is like or comparable to the structure of implant 10. Accordingly, discussion of the like components is not believed necessary. The superior and inferior surfaces 14, 16 of implant 10 are flat planar surfaces. As seen best in FIG. 5, superior and inferior surfaces 14, 16 of implant 40 are curved surfaces which still retain the wedge-shaped profile. The curved surfaces of superior and inferior surfaces 14, 16 of implant 40 are a mirror-image of the topography of the vertebral end plates. Thus, the curved surfaces conform to the contours of the end plates.

FIG. 6 shows a top view of a third embodiment of an implant 50 according to the present invention. In general, most of the structure of implant 50 is like or comparable to the structure of implants 10, 40. Accordingly, discussion of the like components is not believed necessary. As best seen in FIG. 7, implant 50 comprises a top portion 52 joined to a bottom portion 54. As it may be difficult to obtain a single section of allogenic bone from which implant 50 is to be made, fabricating implant 50 in two pieces, i.e. top and bottom portions 52, 54, allows smaller sections of allogenic bone to be used. A top connecting surface 56 and a bottom connecting surface 58 define the interface between top and bottom portions 52, 54. As shown in FIGS. 8A and 8B, top and bottom surfaces 56, 58 have ridges 60 that mate with grooves 62 to interlock top and bottom portions 52, 54. Preferably, ridges 60 and grooves 62 are formed by milling top and bottom surfaces 56, 58 in a first direction and then milling a second time with top and bottom surfaces 56, 58 oriented 90° with respect to the first direction.

A pin 64 passing through aligned holes 66 in top and bottom portions 52, 54 serves to retain top and bottom portions 52, 54 together. Although pin 64 can be made of any biocompatible material, pin 64 is preferably made of allogenic bone. The number and orientation of pins 64 can be varied.

Figure 11:
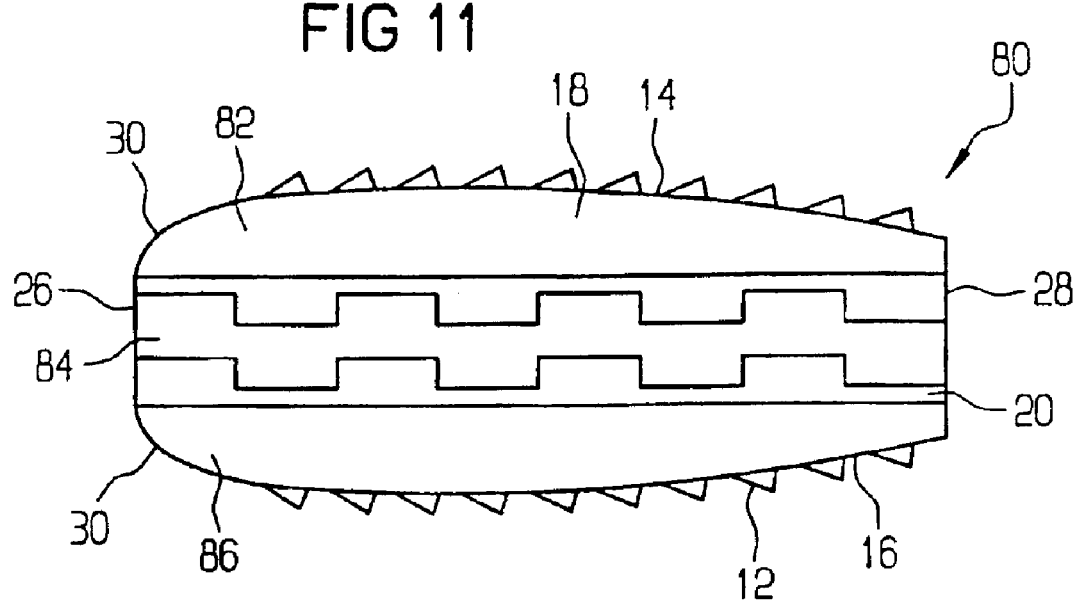
FIG. 11 is a side view of an embodiment of the implant similar to the embodiment of FIGS. 6–8.

FIG. 11 shows an embodiment of an implant 80 which, like implant 50, is made in multiple pieces. In general, most of the structure of implant 80 is like or comparable to the structure of implants 10, 40, 50. Accordingly, discussion of the like components is not believed necessary. Implant 80 has a top portion 82, a middle portion 84, and a bottom portion 86. As was the case for implant 80, the surfaces between the portions are mating surfaces with interlocking surface features, such as ridges and grooves. One or more pins preferably hold top, middle, and bottom portions 82, 84, 86 together.

FIG. 9 shows a perspective view of a fourth embodiment of a first implant 70 according to the present invention. A second implant 70', which is substantially similar to first implant 70, is also shown. In general, most of the structure of first and second implants 70, 70' is like or comparable to the structure of implants 10, 40, 50. Accordingly, discussion of the like components is not believed necessary. First lateral sides 18 of first and second implants 70, 70' are scalloped to have a C-shape. When first and second implants 70, 70' are placed side by side with the first lateral sides 18 facing each other, a cylindrical space 72 is formed. When first and second implants 70, 70' are implanted together, cylindrical space 72 can be filled with osteoconductive material to help promote the formation of new bone. First and second implants 70, 70' can be provided with locking pins 74 which engage apertures 76 to maintain the spatial relationship between first and second implants 70, 70'.

Figure 13:
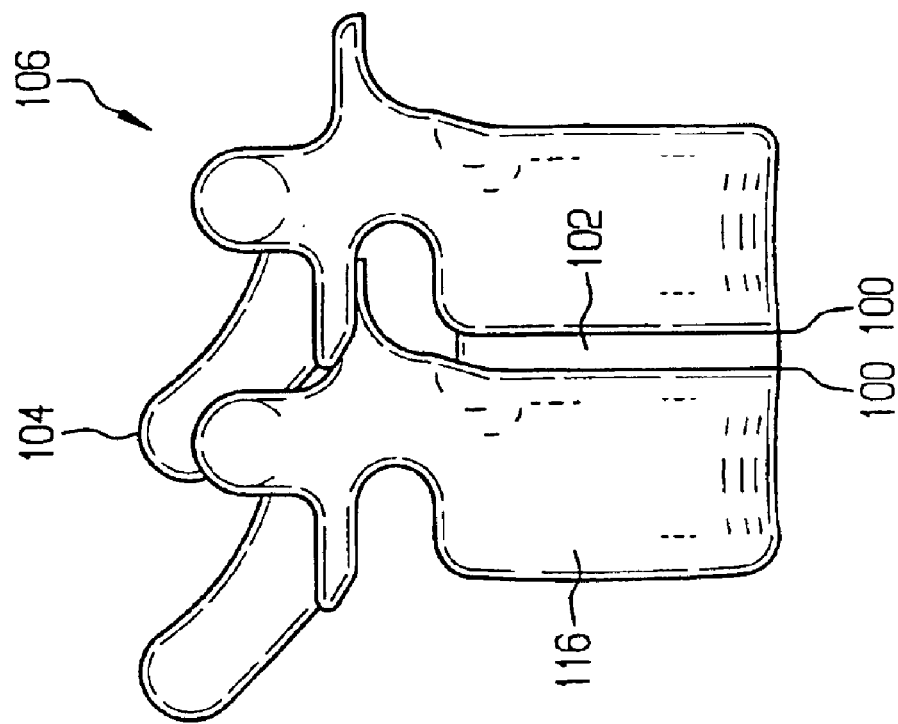
FIG. 13 is a side view of sequentially aligned vertebral bones, such as are found in the cervical, thoracic, or lumbar spine.
Figure 12:
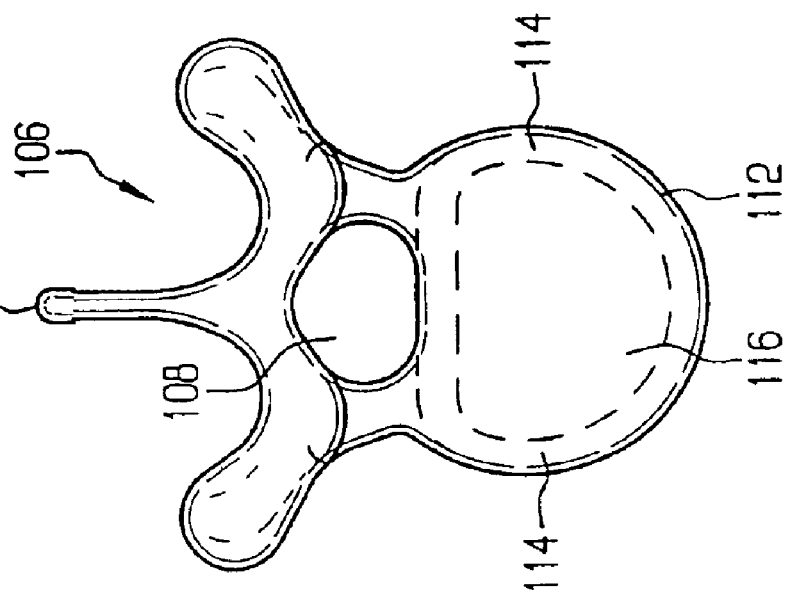
FIG. 12 is a top view of a vertebral bone characteristic of those of the cervical, thoracic, and lumbar spine.
Figure 14:
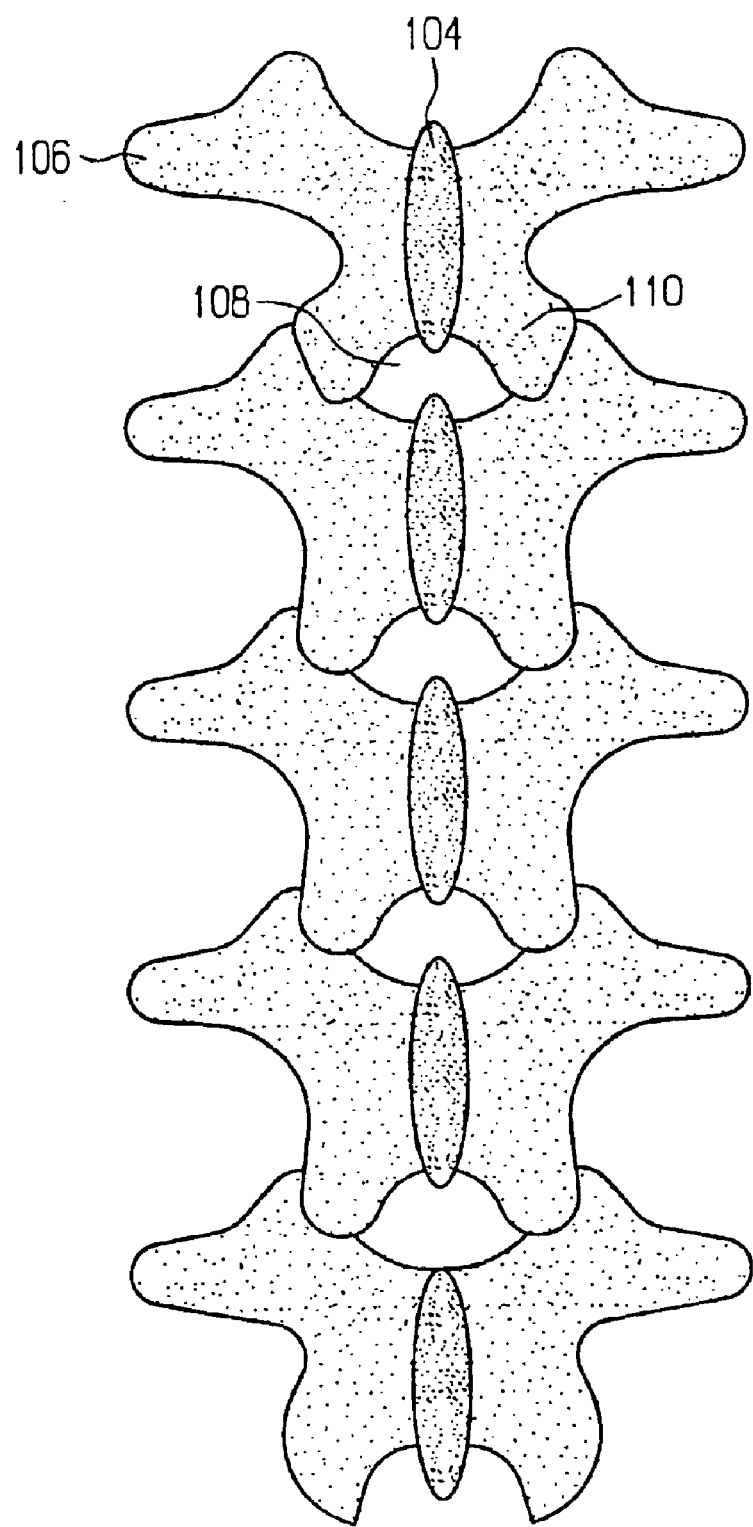
FIG. 14 is a posterior view of a sequence of vertebrae.

The use of the implant according to the present invention will now be described with reference to FIGS. 12–14 and using posterior lumbar interbody fusion as an example. As the implant according to the present invention conforms in size and shape to a portion of end plates 100, preoperative planning is recommended for proper sizing. Determine the appropriate implant height by measuring adjacent intervertebral discs 102 on a lateral radiograph. The implant must be seated firmly with a tight fit between end plates 100 when the segment is fully distracted. The tallest possible implant should be used to maximize segmental stability. Due to variability in degrees of magnification from radiographs, the measurements are only an estimate.

With the patient in a prone position on a lumbar frame, radiographic equipment can assist in confirming the precise intraoperative position of the implant. The surgeon incises and dissects the skin from the midline laterally and locates spinous process 104, lamina 106, dura 108, and nerve roots of the appropriate level(s). As much as facets 110 as possible should be preserved to provide stability to the intervertebral segment. The surgeon performs a laminotomy to the medial aspect of facet 110 and reflects dura 108 to expose an approximately 13 mm window to the disc space. Disc 102 is removed through the window until only anterior 112 and lateral 114 annulus remain. The superficial layers of the entire cartilaginous end plates 100 are also removed to expose bleeding bone. Excessive removal of the subchondral bone may weaken the anterior column. Furthermore, if the entire end plate is removed, this may result in subsidence and a loss of segmental stability.

Distraction can be done with either a surgical distractor or a trial spacer implant. In the first method, the distractor blades are placed into the disc space lateral to dura 108. The curve on the neck of the distractor should be oriented toward the midline. The distractor blades should be completely inserted into the disc space so that the ridges at the end of the blades rest on vertebral body 116. Fluoroscopy can assist in confirming that the distractor blades are parallel to end plates 100. Correct placement will angle the handles of the distractor cranially. particularly at L5-S1. The handle of the distractor is squeezed to distract the innerspace. The distraction is secured by tightening the speed nut on the handle.

Using the preoperatively determined size, a trial spacer is inserted in the contralateral disc space with gentle impaction. Fluoroscopy and tactile judgement can assist in confirming the fit of the trial spacer until a secure fit is achieved. Using either the slots or threader hole on the implant, the selected implant is inserted in the contralateral disc space. Alternatively, the channels on the implant allow distraction and insertion to occur on the same side. Regardless of the side the implant is inserted in, autogenous cancellous bone or a bone substitute should be placed in the anterior and medial aspect of the vertebral disc space prior to placement of the second implant. The distractor is removed and a second implant of the same height as the first implant is inserted into the space, using gentle impaction as before. Preferably, the implants are recessed 2–4 mm beyond the posterior rim of the vertebral body.

Figure 15:
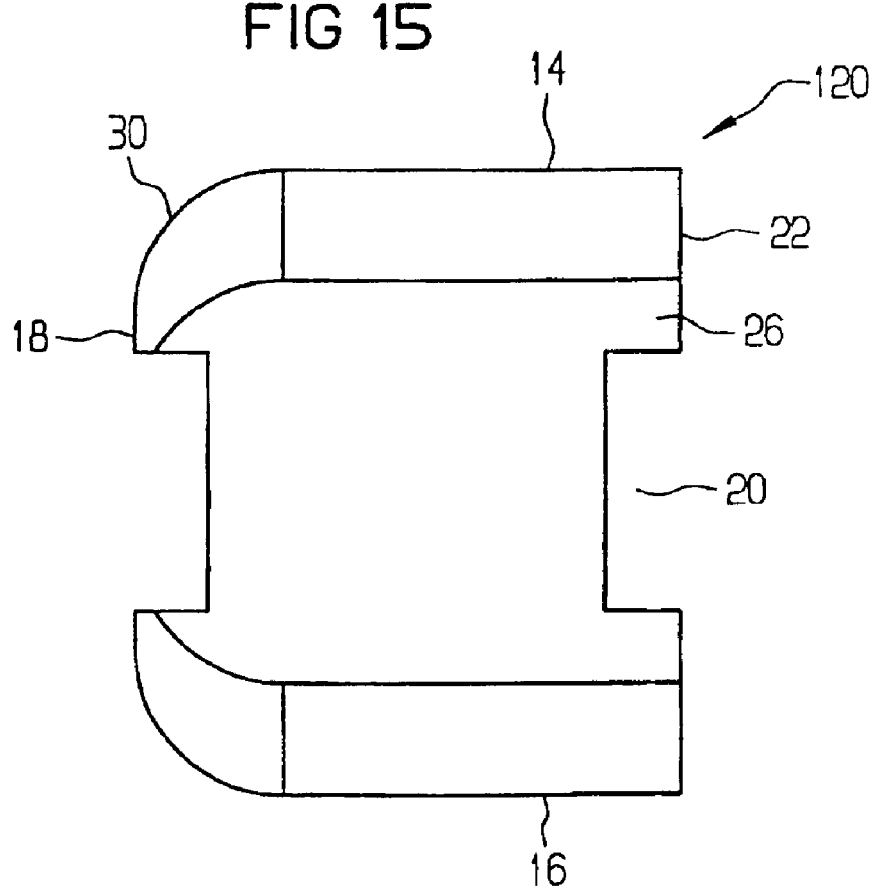
FIG. 15 is an end view of another embodiment of the implant.

As previously noted, the implant according to the present invention can be inserted using minimally invasive procedures. In some of these procedures, only one side of the spinal cord needs to be approached. This minimizes muscle stripping, scar tissue in the canal, and nerve root retraction and handling. In clinical situations in which bilateral implant placement is required, proper implantation on the side opposite the incision can be difficult. FIG. 15 shows a beveled spacer 120 that facilitates placement on the side contralateral to the incision. In general and unless otherwise described, most of the structure of beveled spacer 120 is like or comparable to the structure of implants 10, 40, 50, and 80. Accordingly, discussion of the like components is not believed necessary. First lateral side 18 transitions to superior and inferior surfaces 14, 16 with rounded edges 30. First lateral side 18 also transitions to anterior and posterior sides 26, 28 with rounded edges 30. Additionally, spacer 120 has no teeth. The lack of teeth and rounded edges 30 enable spacer 120 to slide between the end plate and across the evacuated disc space (from one lateral annulus to the other) to the contralateral side. As first lateral side 18 is the side that must promote movement of spacer 120, the use of rounded edges 30 on second lateral side 22 is optionally. Once spacer 120 has been placed on the side contralateral to the single incision using a surgical instrument to push spacer 120, bone graft or other osteoconductive material is packed in the disc space. Finally, an implant (any of implant 10, 40, 50, 70, or 70' can be used) is implanted in the side proximal to the incision.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An intervertebral implant comprising a plug of allogenic bone conforming in size and shape with a portion of the end plates of adjacent vertebrae, wherein the top and bottom surfaces of the implant include a plurality of teeth provided in at least a two dimensional array with the teeth being spaced apart from one another for interlocking with the adjacent vertebrae, and wherein the teeth have a pyramidal shape profile defined by four sides meeting together to form a tip; wherein the sides opposite each other form an acute angle of approximately 60 degrees at the tip.

2. The implant of claim 1 wherein the implant has an interior space for receiving osteoconductive material to promote the formation of new bone.

3. The implant of claim 2 wherein the osteoconductive material comprises bone chips.

4. The implant of claim 1 wherein the implant has a wedge-shaped profile to help restore disc height and spine curvature.

5. The implant of claim 1 wherein the implant is formed of more than one piece of allogenic bone.

6. The implant of claim 1 wherein the top and bottom surfaces are curved surfaces.

7. The implant of claim 1 wherein the teeth are integral with the top and bottom surfaces.

8. The implant of claim 1 wherein the teeth on the top and bottom surfaces are interrupted to form a channel to receive an insertion instrument for placing the implant.

9. A method for restoring disc height between adjacent vertebrae having facing endplates, the method comprising:
  removing at least a portion of a disc located between the adjacent vertebrae;
  distracting an inner space between the facing endplates; and
  inserting the implant of claim 1 into the distracted inner space.

10. The method of claim 9 further comprising measuring a distance between the adjacent vertebrae with a preoperative lateral radiograph to determine an implant height.

11. The method of claim 9 wherein a distractor is used to distract the inner space.

12. The method of claim 11 further comprising inserting a trial spacer implant to determine an implant height.

13. The method of claim 9 wherein the implant further includes an interior space arid the method further comprises placing osteoconductive material into the interior space of the implant.

14. An implant for restoring disc height between adjacent vertebrae having facing endplates comprising an annular plug of allogenic bone surrounding an interior space, the plug having top and bottom surfaces configured and adapted in use to face the endplates of adjacent vertebrae, wherein the top and bottom surfaces include a plurality of teeth provided in at least a two dimensional array, and wherein the teeth have a pyramidal shape defined by four sides meeting together to form a tip; wherein the sides opposite each other form an acute angle of approximately 60 degrees at the tip.

15. The implant of claim 14 wherein the implant has a wedge-shaped profile to help restore disc height and spine curvature.

16. The implant of claim 15 wherein the top and bottom surfaces are curved surfaces.

17. The implant of claim 14 wherein the teeth are integral with the top and bottom surfaces.

18. The implant of claim 14 wherein the implant is formed of more than one piece of allogenic bone.

19. An intervertebral implant comprising at least one piece of allogenic bone provided with a hollow interior space, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides meeting together to form a tip; wherein the sides apposite each other form an acute angle at the tip; the implant further comprising a pair of parallel channels extending along the entire length of the implant, the channels being substantially smooth, devoid of teeth, and being adapted and configured to receive a single surgical instrument.

20. The implant of claim 19, wherein the top and bottom surfaces each have an opening communicating with the hollow interior space.

21. The implant of claim 19, wherein the interior space and openings form a substantially cylindrical chamber.

22. The implant of claim 19, wherein the angle is approximately 60°.

23. The implant of claim 19, wherein the implant is substantially symmetrical about a mid-plane of the implant.

24. The implant of claim 23, wherein the implant has a wedge shaped profile such that the top surface is inclined with reaped to the bottom surface.

25. The implant of claim 24, wherein the angle of inclination between the top surface and the midplane is between about 4.2° and about 15°.

26. The implant of claim 25, wherein the top and bottom surfaces are substantially flat planar surfaces.

27. The implant of claim 25, wherein the top and bottom surfaces are curved surfaces.

28. The implant of claim 19, wherein the implant has first and second sides and a gradual decrease in height from the first side to the second side.

29. The implant of claim 19, wherein the implant has at least one rounded edge between the top and bottom surfaces to facilitate insertion of the implant.

30. The implant of claim 19, further comprising at least two lateral sides wherein the channels are formed in the two lateral sides.

31. The implant of claim 19, wherein the implant is formed of more than one piece of bone.

32. The implant of claim 31, wherein the pieces of bone are arranged side by side and the top and bottom surfaces are formed of more than one piece of bone.

33. The implant of claim 19, wherein the teeth are arranged to cover substantially the entire top and bottom surfaces.

34. An intervertebral implant formed of at least one piece of allogenic bone provided with a hollow substantially cylindrical interior space, the implant comprising: a midplane about which the implant is substantially symmetrical;
  top and bottom surfaces configured and adapted in use to face the end plates of adjacent vertebrae, the top and bottom surface each having an opening communication with the substantially cylindrical space, and the top surface being inclined in a range between about 4.2° and about 15° with respect to the mid-plane;
  at least two substantially smooth parallel channels adapted and configured to receive a surgical instrument; and
  at least one rounded edge between the top and bottom surfaces to facilitate insertion of the implant;
  wherein the top and bottom surfaces comprise a plurality of teeth provided in a plurality of adjacent rows, and further wherein the teeth are defined by four sides, at least three of the sides forming an acute angle with respect to the respective top and bottom surfaces.

35. The implant of claim 34, wherein the top and bottom surfaces are substantially flat planer surfaces.

36. The implant of claim 34, wherein the top and bottom surfaces are substantially flat in a first direction and curved in a second direction.

37. The implant of claim 34 formed of more than one piece of allogenic bone arranged side by side and adapted and configured such that the top and bottom surfaces are formed of more than one piece of bone.

38. The implant of claim 34, wherein the top and bottom surfaces are curved.

39. An intervertebral implant comprising a plug of allogenic bone conforming in size and shape with a portion of the end plates of adjacent vertebrae, wherein the top and bottom surfaces of the implant include a plurality of teeth provided in at least a two dimensional array with the teeth being spaced apart from one another for interlocking with the adjacent vertebrae, and wherein the teeth have a pyramidal shape profile defined by four sides forming an acute angle with respect to the respective top and bottom surfaces of the implant;

wherein the implant has a wedge-shaped profile such that the top surface is inclined with respect to the bottom surface at an angle of inclination of between about 4° and about 15° to help restore disc height and spine curvature.

40. An intervertebral implant comprising a plug of allogenic bone conforming in size and shape with a portion of the end plates of adjacent vertebrae, wherein the top and bottom surfaces of the implant include a plurality of teeth provided in at least a two dimensional array with the teeth being spaced apart from one another for interlocking with the adjacent vertebrae, and wherein the teeth have a pyramidal shape profile defined by four sides forming an acute angle with respect to the respective top and bottom surfaces of the implant;

wherein the implant is formed of more than one piece of allogenic bone.

41. The implant of claim 41, wherein the implant is formed of at least two pieces of bone and at least two pieces are connected by pins.

42. The implant of claim 42, wherein the pieces of bone are arranged side by side and the top and bottom surfaces are formed of more than one piece of bone.

43. An intervertebral implant comprising a plug of allogenic bone conforming in size and shape with a portion of the end plates of adjacent vertebrae, wherein the top and bottom surfaces of the implant include a plurality of teeth provided in at least a two dimensional array with the teeth being spaced apart from one another for interlocking with the adjacent vertebrae, and wherein the teeth have a pyramidal shape profile defined by four sides forming an acute angle with respect to the respective top and bottom surfaces of the implant;

wherein the top and bottom surfaces are curved surfaces.

44. A method for restoring disc height between adjacent vertebrae having facing endplates, the method comprising:

measuring a distance between the adjacent vertebrae with a preoperative lateral radiograph to determine an implant height;

removing at least a portion of a disc located between the adjacent vertebrae; distracting an inner space between the facing endplates; and inserting an intervertebral implant into the distracted inner space, the implant comprising a plug of allogenic bone conforming in size and shape with a portion of the end plates of adjacent vertebrae, wherein the top and bottom surfaces of the implant include a plurality of teeth provided in at least a two dimensional array with the teeth being spaced apart from one another for interlocking with the adjacent vertebrae, and wherein the teeth have a pyramidal shape profile defined by four sides fanning an acute angle with respect to the respective lop and bottom surfaces of the implant.

45. An implant for restoring disc height between adjacent vertebrae having facing endplates comprising an annular plug of allogenic bone surrounding an interior space, the plug having top and bottom surfaces configured and adapted in use to face the endplates of adjacent vertebrae, wherein the top and bottom surfaces include a plurality of teeth provided in at least a two dimensional array, and wherein the teeth have a pyramidal shape defined by four sides forming an acute angle with respect to the respective top and bottom surfaces of the implant;

wherein the implant is formed of more than one piece of allogenic bone.

46. An intervertebral implant comprising at least one piece of allogenic bone provided with a hollow interior space, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides forming an acute angle with respect to the respective top and bottom surfaces of the implant;

wherein:

the implant is substantially symmetrical about a midplane of the implant; and the implant has a wedge shaped profile such that the top surface is inclined with respect to the bottom surface, an angle of inclination between the top surface and the midplane is between about 4.2° and about 15°.

47. The implant of claim 46, wherein the top and bottom surfaces are substantially flat planar surfaces.

48. The implant of claim 46, wherein th top and bottom surfaces are curved surfaces.

49. An intervertebral implant comprising at least one piece of allogenic bone provided with a hollow interior space, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides meeting together to form a tip; wherein the sides opposite each other form an acute angle of approximately 60° at the tip;

wherein the implant has first and second sides and a gradual decrease in height from the first side to the second side.

50. An intervertebral implant comprising at least one piece of allogenic boric provided with a hollow interior space, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides meeting together to form a tip; wherein the sides opposite each other form an acute angle of approximately 60° at the tip;

wherein the implant has at least one rounded edge between the top and bottom surfaces to facilitate insertion of the implant.

51. An intervertebral implant comprising:

at least one piece of allogenic bone provided with a hollow interior space, the implant having top and bottom surfaces configured and adapted in use to face the end plates of adjacent vertebrae; and a pair of parallel channels adapted and configured to receive a single surgical instrument;

wherein:

the top and bottom surfaces include a plurality of teeth provided in a plurality of adjacent rows, and wherein at least a portion of the teeth have a pyramidal shape defined by four sides forming an acute angle with respect to the respective top and bottom surfaces of the implant; and at least one channel extends along the entire length of the implant and is substantially devoid of teeth.

52. The implant of claim 51, further comprising at least two lateral sides wherein the channels are formed in the two lateral sides.

53. An intervertebral implant comprising at least one piece of allogenic bone provided with a hollow interior spare, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides forming an acute angle with respect to the respective top and bottom surfaces of the implant;

wherein the implant is formed of more than one piece of bone.

54. The implant of claim 53, wherein the implant is formed of at least two pieces of bone and at least two pieces are connected by pins.

55. The implant of claim 54, the pieces of bone are arranged side by side and the top and bottom surfaces are formed of more than one piece of bone.

56. An implant for restoring disc height between adjacent vertebrae having facing endplates comprising an annular plug of allogenic bone surrounding an interior space, the plug having top and bottom surfaces configured and adapted in use to face the endplate of adjacent vertebrae, wherein the top and bottom surfaces include a plurality of teeth provided in at least a two dimensional array, and wherein the teeth have a pyramidal shape defined by four sides forming an acute angle with respect to the respective top and bottom surfaces of the implant;

wherein:

the angle formed from the tip of the teeth to a base where the sides meet with the respective top and bottom surfaces is approximately 60 degrees; and the implant bas a wedge-shaped profile to help restore disc height and spine curvature.

57. The implant of claim 56 wherein the top and bottom surfaces are curved surfaces.

58. An intervertebral implant comprising at least one piece of allogenic bone provided with a hollow interior space, the implant having top and bottom surfaces configured and adapted in use to face the end plates of adjacent vertebrae, wherein the top and bottom surfaces include a plurality of teeth provided in a plurality of adjacent rows, and wherein at least a portion of the teeth have a pyramidal shape defined by four sides forming an acute angle with respect to the respective top and bottom surfaces of the implant;

wherein the angle formed from the tip of the pyramidal teeth to a base where the sides meet with the respective top arid bottom surfaces is approximately 60°.

* * * * *